United States Patent [19]

Melton, Jr. et al.

[11] Patent Number: 5,375,600
[45] Date of Patent: Dec. 27, 1994

[54] ULTRASONIC FREQUENCY-DOMAIN SYSTEM AND METHOD FOR SENSING FLUID FLOW

[75] Inventors: Hewlett E. Melton, Jr., Montclair; King-Wah W. Yeung, Cupertino; Michael Greenstein, Los Altos, all of Calif.

[73] Assignee: Hewlett-Packard Company, Palo Alto, Calif.

[21] Appl. No.: 104,309

[22] Filed: Aug. 9, 1993

[51] Int. Cl.$^5$ ................................................ A61B 8/06
[52] U.S. Cl. .............................. 128/661.09; 73/861.25
[58] Field of Search ...................... 128/661.07–661.10, 128/660.05; 73/861.25

[56] References Cited

U.S. PATENT DOCUMENTS

| | | | |
|---|---|---|---|
| 5,121,364 | 6/1992 | O'Donnell | 128/660.06 |
| 5,156,153 | 10/1992 | Bonnefous | 128/661.09 |
| 5,249,577 | 10/1993 | Shinomura et al. | 128/661.09 X |

OTHER PUBLICATIONS

Bodily, K. C. et al "Spectral Analysis of Doppler Velocity Patterns in Normals & Patients w/Carotid Artery Stenosis", Clin. Phys. (1981) v. 1 pp. 365–374.

*Primary Examiner*—Francis Jaworski
*Attorney, Agent, or Firm*—Jeffrey Slusher

[57] ABSTRACT

Pulses of ultrasound are focused in the patient's body to create an interrogation volume where a characteristic of blood flow is to be measured. The bandwidth of the back-scattered Doppler return signal is measured. In order to measure flow velocity independent of direction, the interrogation volume is generated substantially as a sphere in which the range dimension is set equal to the lateral dimensions (azimuth and elevation) of the interrogation signal. The Doppler bandwidth is then scaled to provide a direction-independent measurement of flow velocity. In order to determine the direction of flow, the interrogation volume is generated substantially as an ellipsoid. The long axis of the ellipsoidal interrogation volume is then rotated until the measured Doppler bandwidth is at a minimum, which is reached when the long axis is aligned with the flow direction. The interrogation volume is preferably rotated and translated using differential phasing of the ultrasonic signals from different transducer elements in a two-dimensional array.

8 Claims, 11 Drawing Sheets

ULTRASONIC FREQUENCY-DOMAIN SYSTEM AND METHOD FOR SENSING FLUID FLOW

BACKGROUND OF THE INVENTION

1. Technical Field

This invention involves a system and a method for using ultrasound to sense the speed and direction of flow of a fluid, such as blood in a coronary artery.

2. Description of the Related Art

The measurement of blood flow in the coronary arteries is a well-known technique for diagnosing coronary artery diseases. There are, consequently, many different devices and methods for determining this blood flow.

One common sensing technique involves the use of ultrasound. Using this technique, ultrasound is directed into the body of the patient and tiny particles such as red blood cells, which are suspended in the blood, scatter the ultrasonic energy back towards the transducer. The transducer then converts the back-scattered ultrasonic energy into an electrical signal that is processed in some known manner to determine an estimate of the flow.

One great advantage of ultrasonic sensing is that it is non-invasive, meaning that it can be carried out without having to cut or insert anything into the patient's body. A problem one faces when using existing ultrasonic flow measurement techniques, however, is that measurements are often made through the "keyhole" between the ribs in a transthoracic scan, where the coronary arteries typically twist over the curved surface of the moving heart wall. The direction of the blood in the arteries or the motion of the heart wall with respect to the line-of-sight of the ultrasonic beam is therefore usually not known. This is a serious problem for the many common techniques that use the principle of Doppler shift.

The Doppler principle used in existing techniques for calculating flow velocity v based on the frequency shift of ultrasonic waves scattered by moving red cells can be expressed as follows:

$$f_d = 2\left(\frac{v}{c}\right) f_0 \cdot \cos\theta,$$

in which $f_0$ is the frequency of the ultrasonic wave sent into the body, v is the flow velocity, c is the speed of sound, $\theta$ is the angle between the line-of-sight direction of the beam and the flow, and $f_d$ is the detected frequency shift of the signal that returns to the transducer. As long as $\cos\theta$ is not equal to zero, the frequency shift will increase with increasing flow velocity.

As the equation shows, it is not possible using conventional Doppler techniques to detect any frequency shift if $\theta$ equals 90°, that is, if the flow is perpendicular to the line-of-sight of the ultrasonic transducer, regardless of how fast the blood is flowing. Police officers who use radar guns to check for speeders are a more common example of this problem: the officers cannot position themselves at right angles to the cars being checked because the typical radar gun uses the same Doppler principle and would tell the disbelieving police officers that the cars were not moving at all.

If the direction of flow is at an angle of 60° from the line-of-sight of the ultrasonic transducer, the indicated frequency shift will be only half what it would be if the flow and the line-of-sight were parallel. In general, the angle $\theta$ is not known beforehand. In the context of blood-flow measurements, what is needed is therefore a technique that is substantially isotropic, that is, direction-independent. Alternatively, a technique is needed that determines the direction of flow so that Doppler measurements can be adjusted accordingly. Furthermore, a system is needed that can implement these techniques. This invention provides such techniques and such a system.

SUMMARY OF THE INVENTION

According to the invention, pulses of ultrasound are focused in the patient's body to create an interrogation volume where blood flow is to be measured. In order to measure flow velocity independent of direction, the interrogation volume is generated substantially as a sphere. This is done by creating an ultrasonic interrogation volume in which the range dimension, which is determined by the number of excitation cycles, is set equal to the lateral dimensions (azimuth and elevation). In particular, an ultrasonic interrogation volume is generated as a region in which the mean power evaluated over any set of orthogonal axes is the same as that of a sphere delimited by a surface where the signal intensity is constant. The Doppler shift of the back-scattered signal is then measured and the bandwidth of this signal is determined and scaled to provide an indication of the magnitude of velocity of blood flow.

In order to determine the direction of flow, the interrogation volume is generated substantially as an ellipsoid. The long axis of the ellipsoidal interrogation volume is then rotated until the measured Doppler bandwidth of the return signal is at a minimum, which is reached when the long axis is aligned with the flow direction. The interrogation volume is preferably rotated and translated using differential phasing of the ultrasonic signals from different transducer elements in a two-dimensional, piezoelectric phased array.

A system according to the invention for measuring fluid flow includes a transducer (preferably a two-dimensional phased array) that is driven by a timer/exciter so as to generate an ultrasonic interrogation signal as a series of phased pulses. The return signal from the interrogation volume is converted back into electrical form either by the transducer or a receiver, or a combination of both. A Doppler detection circuit is connected to the transducer and receiver to sense the Doppler shift of the return signal and to generate a Doppler signal as its output. A bandwidth detection circuit receives the Doppler signal, calculates the bandwidth of this signal, and generates as its output either a Doppler bandwidth signal, which is used by a processor to calculate flow velocity, or a signal that is scaled to indicate velocity directly.

DETAILED DESCRIPTION

This invention provides a method and a system for determining the speed and direction of flow of a fluid within any conduit as long as the fluid contains some form of particles or discontinuities that are able to scatter ultrasonic waves. The invention is, however, particularly well suited for solving the problems, described above, that are connected with determining the speed and direction of flow of blood within a blood vessel such as a coronary artery, and also within other organs of the body. Accordingly, the discussion below is directed to this application.

Figure 1:
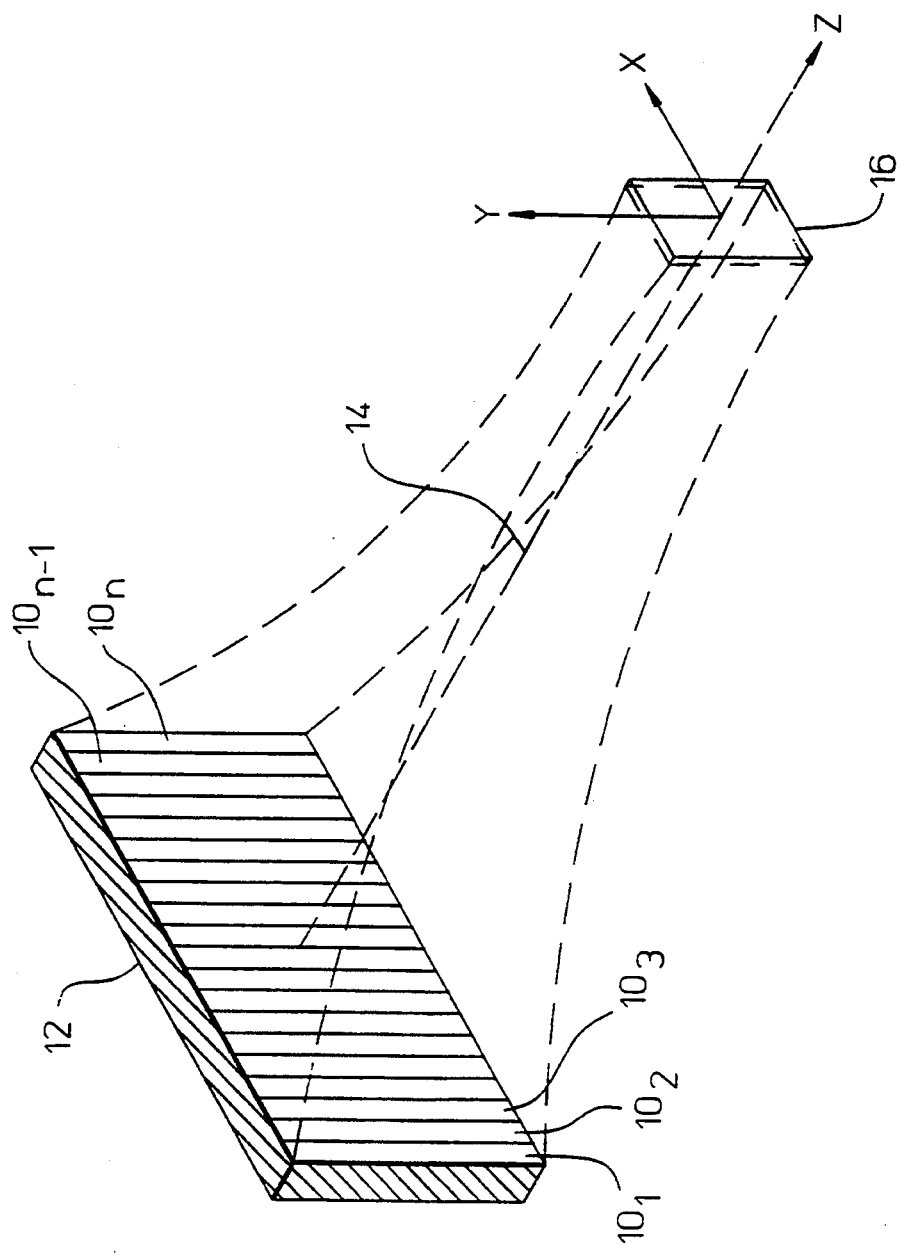
FIG. 1 illustrates an anisotropic interrogation volume (AIV) generated by a 1-D phased array of ultrasonic transducer elements as found in the prior art.

FIG. 1 illustrates the principle of operation of a conventional one-dimensional phased array of ultrasonic transducer elements that are used to estimate fluid flow. In such devices, several ultrasonic transducer elements $10_1, 10_2, 10_3, \ldots, 10_{n-1}, 10_n$ are mounted or manufactured as a parallel array 12. The transducer elements are individually excited using known circuitry and techniques to generate a pattern of ultrasonic waves that propagate principally along an interrogation direction 14, which can be steered over a range of angles relative to the normal to the plane of the phased array 12.

The signals from the various transducer elements $10_1, \ldots, 10_n$ are phased using known techniques so that they focus to create a region of maximum constructive interference where one wishes to measure the fluid flow. This region in known as the interrogation volume. In FIG. 1, the anisotropic interrogation volume (AIV) created by such a conventional 1-D phased array 12 is indicated as the thin, substantially rectangular AIV region 16.

Existing ultrasonic imaging techniques such as the one illustrated in FIG. 1 employ bursts of ultrasonic waves with the shortest possible duration in order to achieve high range resolution in the image. Because the lateral dimensions of the ultrasonic beam are limited by the physical dimensions of the transducer elements $10_1, 10_2, \ldots, 10_n$, these techniques often cause the anisotropism, that is, the direction-dependence, of the interrogation volume 16.

In FIG. 1, the boundaries of the ultrasonic beam are shown as the −6 dB boundaries of the intensity of the interrogation signal and the lengths of the "edges" are not equal. Other power levels for the boundary may of course be chosen; the properties of the interrogation volume created by the interrogation signal are discussed in greater detail below. For typical conventional systems with the configuration illustrated in FIG. 1, the range dimension (z-axis) of the interrogation volume 16 is typically less than 1 mm because of the short pulse length used, while the azimuthal dimension (x-axis) is about 3 mm and the dimension in the elevational direction (y-axis) is roughly 5 mm.

The anisotropism of the conventional interrogation volume causes the signal returned to the transducer elements to have characteristics that depend on the orientation of the interrogation beam and the direction of flow of the fluid to be measured. In other words, if the fluid is flowing in the x-direction, the system will indicate that its speed is different than if it were flowing in the z-direction, even if the speed is the same. The cause of this problem is discussed above when it comes to the Doppler techniques commonly used.

Figure 2:
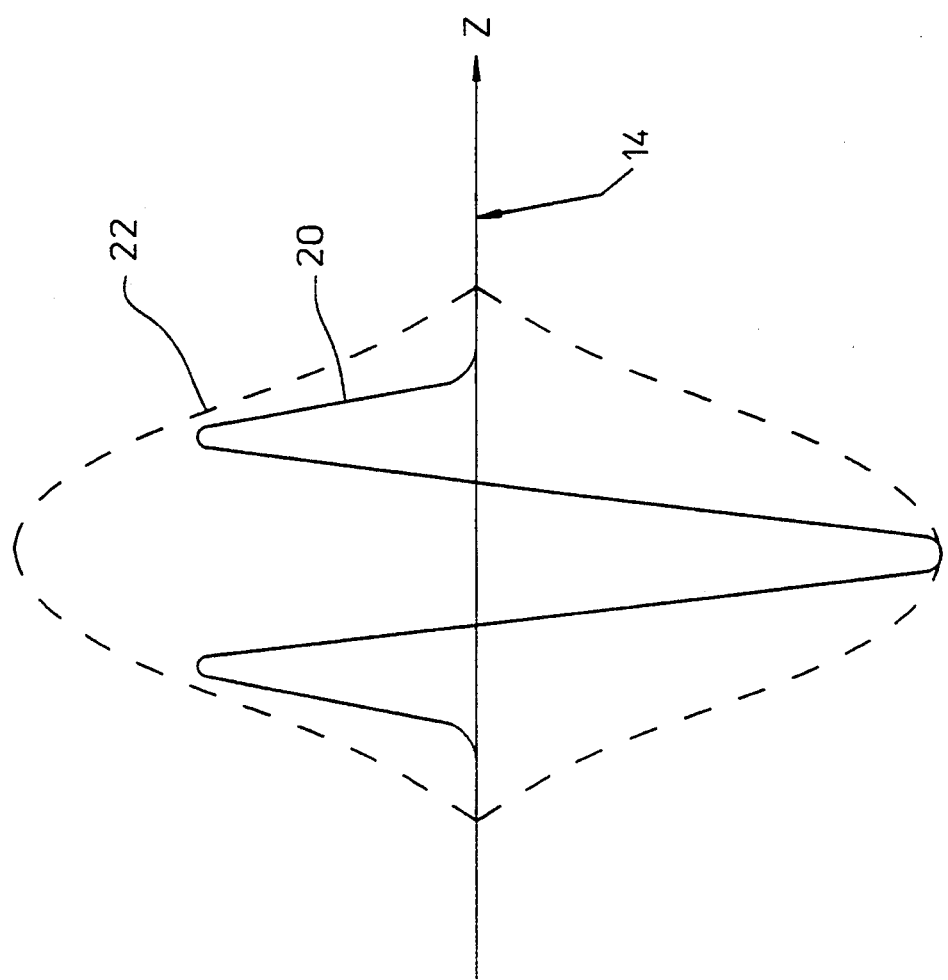
FIG. 2 illustrates a wave and envelope for a conventional anisotropic interrogation volume (AIV).

FIG. 2 shows a wave and envelope along the range direction (z-axis) used to produce an AIV. In order to increase image resolution, a typical conventional imaging transducer with an AIV has only one or two cycles within the interrogation volume. In FIG. 2, 1½ cycles of the interrogation pulse 20 define the wave envelope 22 of the AIV.

As is well known, the pulse 20 will be scattered back towards the transducer array 12 (FIG. 1) by each of the particles within the fluid, such as red blood cells in an artery. The back-scattered pulses thereby undergo Doppler shift. Using the Doppler relationship shown above, the degree of frequency shift is then used to calculate fluid flow. As is discussed above, however, the degree of frequency shift in such conventional systems depends on the angle between the direction of fluid flow and the interrogation direction 14.

In ultrasonic flow-measuring systems, the waves of ultrasound are typically transmitted at a constant pulse repetition frequency (PRF); this is also preferred according to this invention since it leads naturally to constant sampling rates for the return signal. The signal that returns to the ultrasonic transducer, either at a fixed time delay or, equivalently, at a fixed distance from the transducer, after the generation of each burst, is produced by the scattering of a large number of particles that lie inside the interrogation volume. In the interrogation volume, the envelope of the ultrasonic signal along the direction of wave propagation is primarily determined from the envelope of the burst (the length) as a function of time; the cross-sectional area is determined by the transducer transmit and receive beam forming in a plane perpendicular to the propagation direction.

Figure 3:
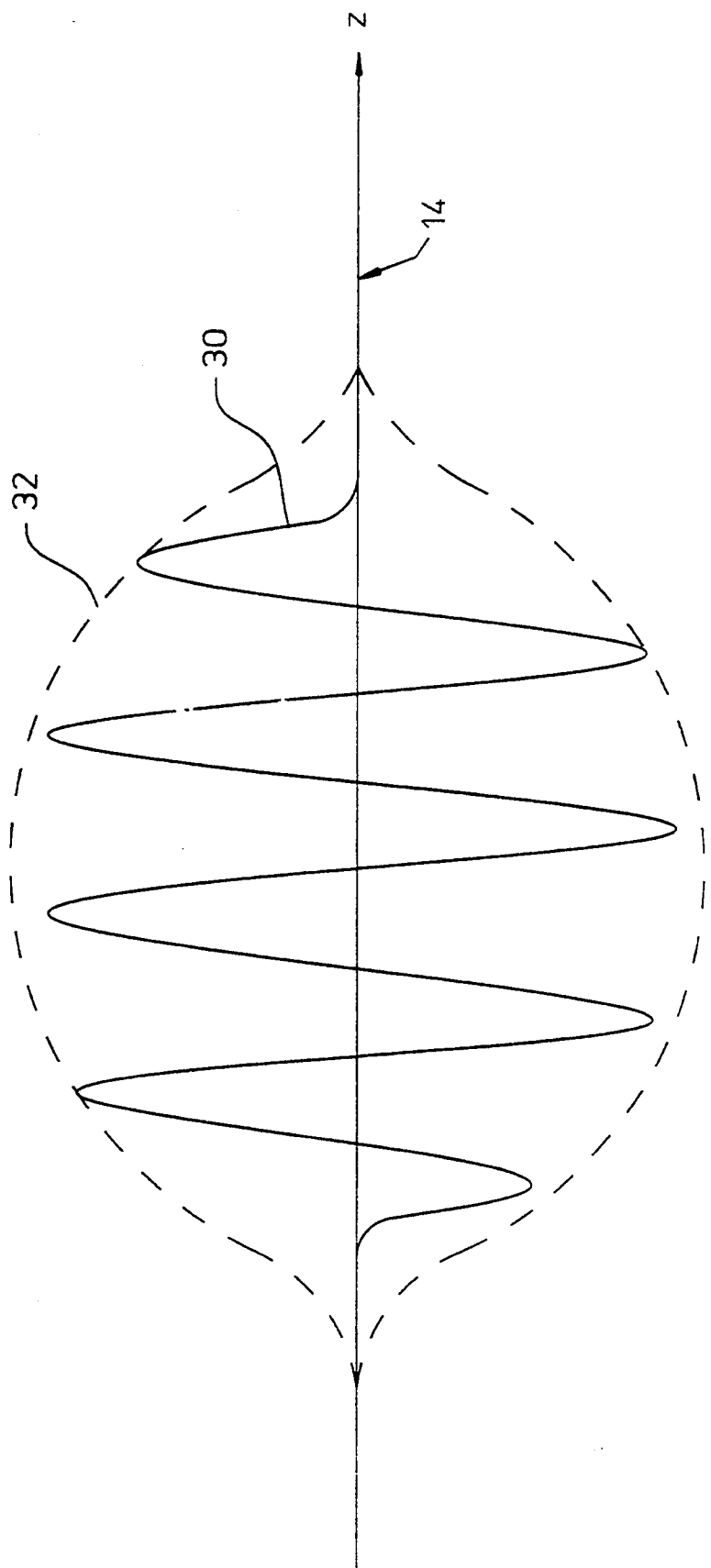
FIG. 3 illustrates a wave and envelope for a spherical interrogation volume (SIV) according to the invention.

FIG. 3 illustrates a wave 30 and envelope 32 of an SIV along the range direction. Four cycles of the wave 30 define the wave envelope 32 along the range dimension of the SIV. In order to give the wave envelope the proper curvature along the z-axis, the amplitude of the pulse 30 must increase from a minimum near the forward and rearmost points of the SIV to a maximum near the center of the SIV. The electrical transmit and receive signals needed to create the waveform for an SIV as shown in FIG. 3 can be determined by experiment or by theoretical calculations based on a knowledge of the physical properties of the chosen transducer elements in any given application.

Figure 4:
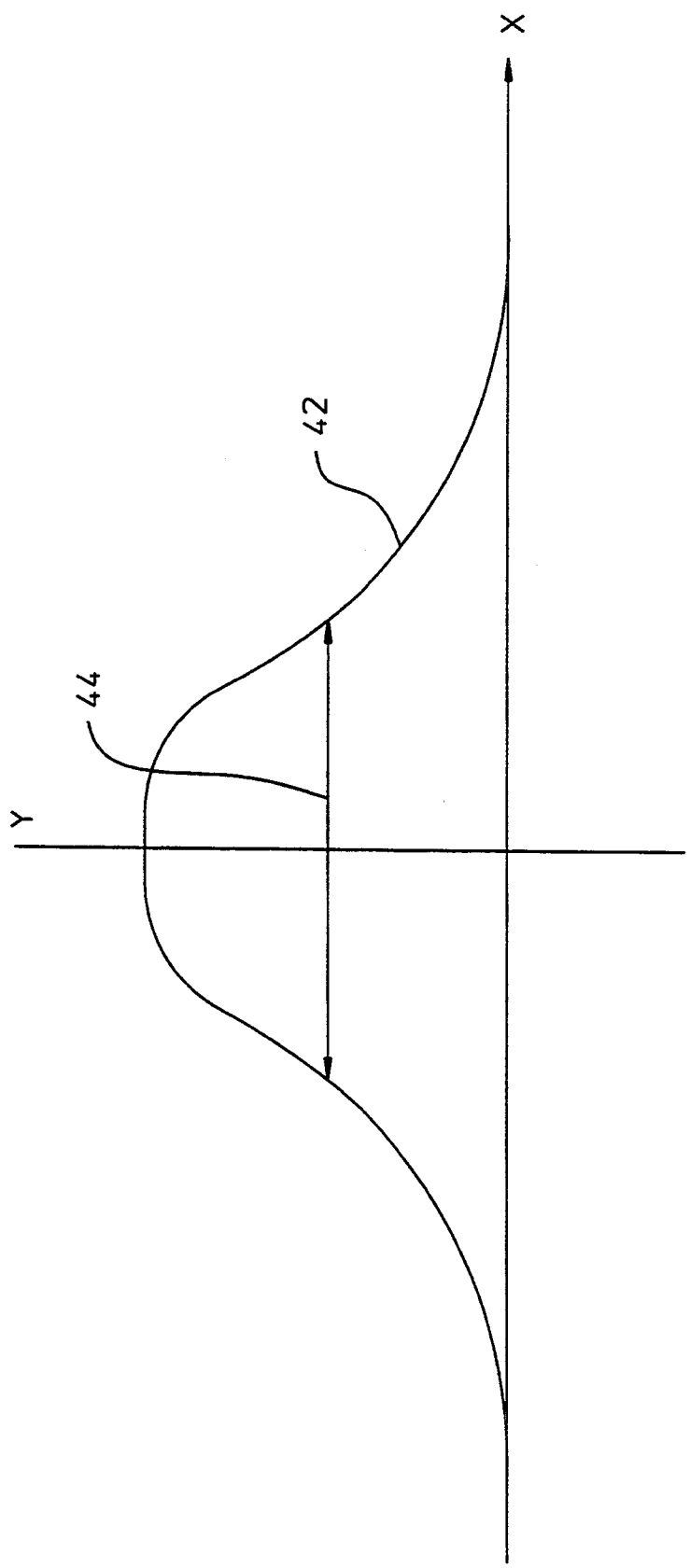
FIG. 4 illustrates a wave envelope for a SIV and an AIV along a lateral direction.

FIG. 4 illustrates a wave envelope for both an AIV and SIV along a lateral direction. As FIG. 4 shows, the beam width for both interrogation volumes is limited by the focussing capability of the transducer. The double arrow 44 indicates the −6 dB width of the wave envelope of the interrogation volume. For a perfect SIV, the envelope of the interrogation signal (and its −6 dB width) along any direction through the center of the SIV remains the same.

It will typically not be possible to create a perfectly spherical interrogation volume; rather, the interrogation volume may have a "tail" or "lip" along one or more of the axes. In general, however, as long as the interrogation volume is substantially spherical, the results will not be distorted significantly; in any event, the substantially spherical interrogation volume according to the invention will provide much greater direction independence than anisotropic interrogation volumes used in the prior art. Experiments have indicated, for example, that a sufficiently spherical interrogation volume can be generated by creating an envelope with a Gaussian range profile of appropriate width. The definition of "spherical" preferred in the invention is discussed below.

According to the invention, the length of the interrogation volume is generated so that it is the same as the width and height of the beam. The interrogation volume is then approximately spherical. As is explained below, the shape of the volume is preferably determined on the basis of mean power, and the spherical interrogation volume (SIV) is thereby made independent of the direction of fluid flow.

Figure 5:
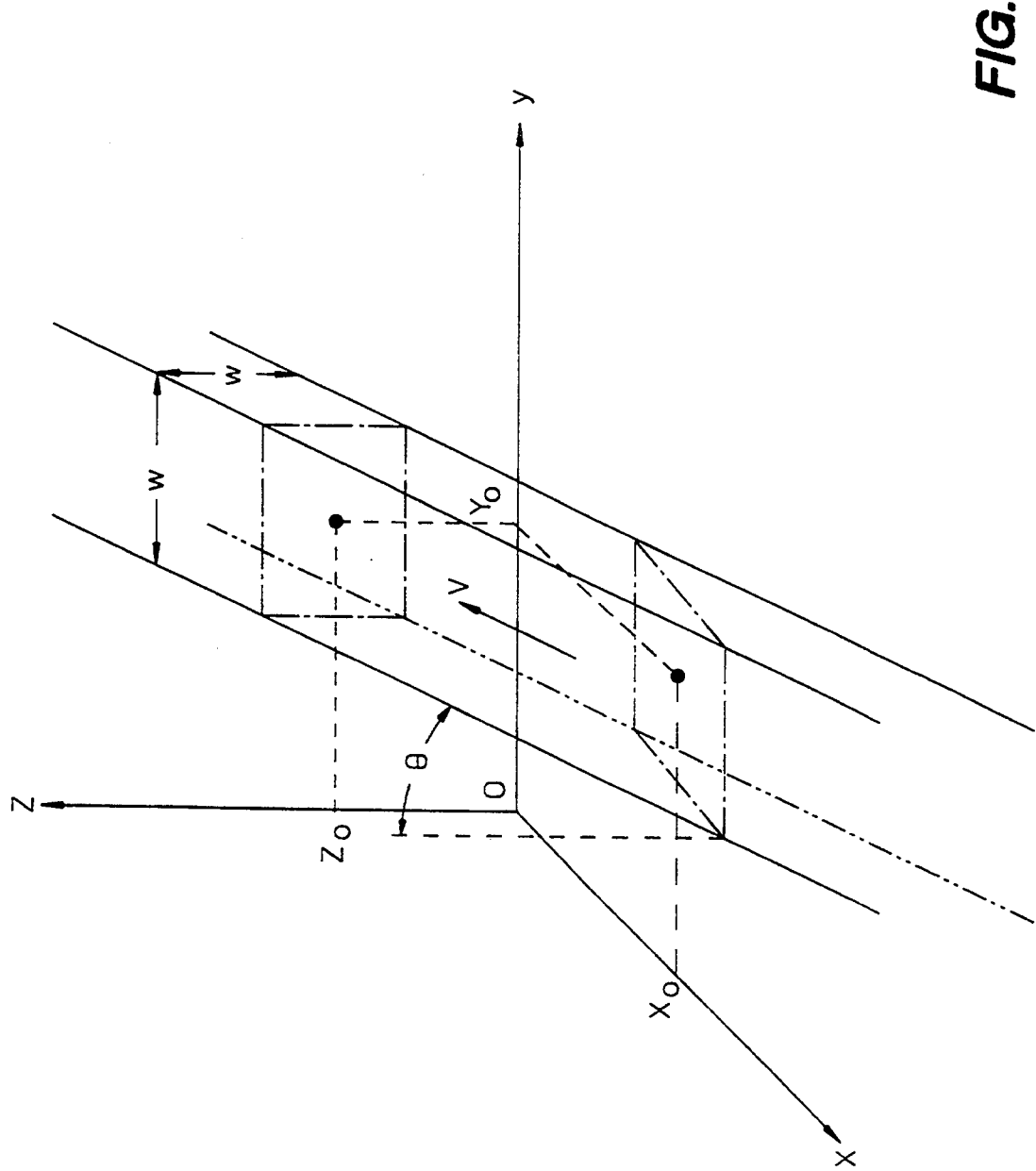
FIG. 5 illustrates a mathematical representation of a volume through which particles are flowing.

FIG. 5 illustrates the theoretical basis for the method according to the invention. Assume particles are travelling with a uniform velocity V (known in the art as "blunt flow") in a vessel that has a W×W square cross section. The impulse response of the interrogation volume centered at (0, 0, 0) is taken to be:

$$h(x,y,t) = K \cdot \exp\left[\frac{-(x^2 + y^2)}{4Y^2}\right] \cdot \exp\left[\frac{-t^2}{4T^2}\right] \cdot \sin\omega_0 t \quad \text{Eqn. 1:}$$

where K is a constant, Y is the beam width, T is the pulse length, and $\omega_0$ is the ultrasonic angular frequency. The autocorrelation function of the return signal produced by the scattering of particles in the interrogation volume that is centered at (0, 0, 0) is given by:

$$r(\tau) = UV_e \cdot \cos(\Omega V \tau \cos\theta) \cdot \quad \text{Eqn. 2:}$$

$$\exp\left[-\tau^2\left(\frac{V^2\sin^2\theta}{8Y^2} + \frac{V^2\cos^2\theta}{8R^2}\right)\right]$$

where U is a constant, $\tau$ is the lag time, $\Omega = 2\omega_0/c$ (c is the velocity of ultrasound in the medium), $R = cT/2$ is the length of the interrogation volume, and the effective volume of the scatterers is $V_e$, which is defined as:

$$V_e = \frac{\pi}{4} \cdot \sqrt{\pi}\ Y^2 R (E_1 - E_2)(E_3 - E_4) \quad \text{Eqn. 3}$$

where

-continued $$E_1 = \text{erf}\left[\frac{Y_0 + \frac{\omega}{2}}{\sqrt{2}\ Y}\right]$$

$$E_2 = \text{erf}\left[\frac{Y_0 - \frac{\omega}{2}}{\sqrt{2}\ Y}\right]$$

$$E_3 = \text{erf}\left[\tan\theta \cdot \frac{z_0 + \frac{\omega}{2\sin\theta}}{\sqrt{2Y^2 + 2R^2\tan^2\theta}}\right]$$

$$E_4 = \text{erf}\left[\tan\theta \cdot \frac{z_0 - \frac{\omega}{2\sin\theta}}{\sqrt{2Y^2 + 2R^2\tan^2\theta}}\right]$$

The Fourier transform of the autocorrelation function is the power spectrum $g(\omega)$:

$$g(\omega) = \frac{UV_e\sqrt{\pi}}{2F} \cdot \quad \text{Eqn. 4:}$$

$$\left\{\exp\left[\frac{-(\omega + \Omega V\cos\theta)^2}{4F^2}\right] + \exp\left[\frac{-(\omega - \Omega V\cos\theta)^2}{4F^2}\right]\right\}$$

where $\omega$ is the angular frequency and F is the bandwidth, which is given by:

$$F = |V|\sqrt{\frac{\sin^2\theta}{8Y^2} + \frac{\cos^2\theta}{8R^2}} \quad \text{Eqn. 5}$$

For a spherical interrogation volume according to the invention, the length R of the interrogation volume is generated so that it is equal to the beam width Y, that is, R=Y. Substituting this into Eqn. 5 one finds the following expression for the bandwidth of the backscattered Doppler signal:

$$F = \frac{|V|}{\sqrt{8}\ Y}$$

The magnitude $|V|$ of the velocity can then be expressed as:

$$|V| = (\sqrt{8}\ Y) \cdot F$$

This shows that the magnitude of the velocity is proportional to the bandwidth F of the Doppler signal and is independent of the direction of flow of blood with respect to the line-of-sight of the ultrasound beam: the expression for $|V|$ holds true for any arbitrary set of orthogonal axes. The proportionality factor relating the magnitude of velocity $|V|$ to the Doppler bandwidth F is $\sqrt{8}\cdot Y$; this factor can be determined beforehand either theoretically, through simulation, or by experiment, since it requires only knowledge of the beam width Y.

Using the invention, one thus excites an ultrasonic transducer with repeated pulses to generate an interrogation volume that is spherical. The back-scattered signal from moving particles within the interrogation volume is sensed and converted into electrical form. The Doppler shift and the bandwidth of the power spectrum of the Doppler signal are then sensed. The bandwidth is then multiplied by the proportionality factor to provide a measurement of the magnitude of the flow velocity; this measurement is independent of the angle between the direction of flow and the line-of-sight of the transducer. Known hardware structures or numerical techniques may be applied to determine the bandwidth.

Figure 6:
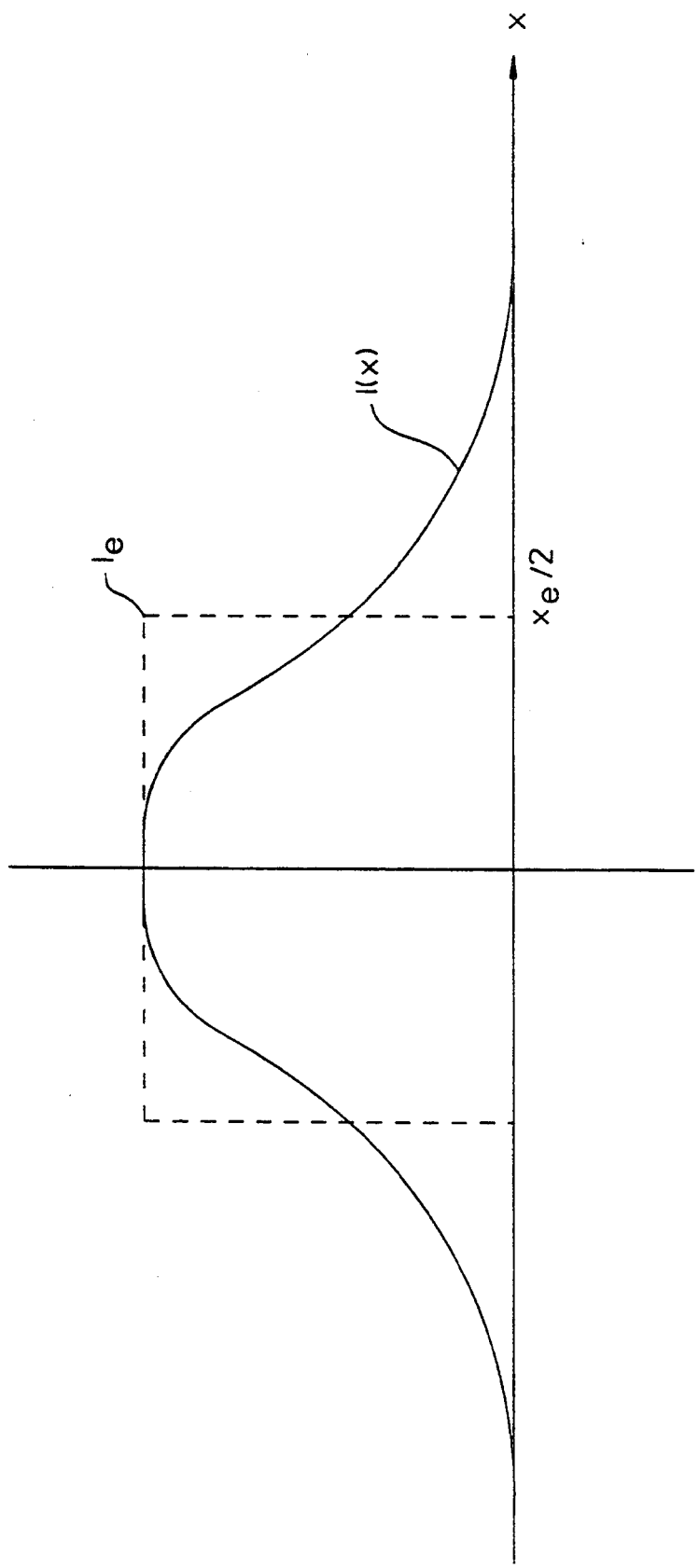
FIG. 6 illustrates a one-dimensional case of replacing an interrogation region with a continuously varying intensity with a matched region with the same effective mean power.

The bandwidth of the power spectrum is thus used to determine the magnitude of velocity. As a result, the definition of the SIV, that is, the meaning of "spherical," used in the invention is preferably made on the basis of mean power. FIG. 6 illustrates this concept for a one-dimensional case.

Assume that an ultrasonic interrogation signal has intensity I(x), which is plotted in FIG. 6 as a function of x. One can then replace this intensity "curve" I(x) with a rectangular region that has the same effective intensity $I_e$ and an effective size $x_e$ so that the area under the rectangle is the same as the area under the curve. Formally, this is equivalent to:

$$\int I(x)dx = I_e x_e \qquad \text{Eqn. 6}$$

Thus, $x_e$ is the dimension that contains the uniform effective intensity $I_e$. In two dimensions, this becomes:

$$\int\int I(x,y)dxdy = I_e \pi R_e^2 \qquad \text{Eqn. 7}$$

where $R_e$ is the effective radius that contains the uniform effective intensity $I_e$.

In the case of three dimensions, which is the case of interest for an SIV as in this invention, this becomes:

$$\int\int\int I(x,y,z)dxdydz = I_e \cdot \frac{4}{3}\pi R_e^2 \qquad \text{Eqn. 8}$$

This equation is valid for any set (x', y', z') that forms a three-dimensional set of orthogonal dimensions. Here, $R_e$ is the radius of the sphere of intensity $I_e$ that contains the same mean power as the integral of I(x,y,z). The definition of the SIV on the basis of mean power thus effectively "replaces" the actual interrogation volume with an effective spherical volume of radius $R_e$.

The previous discussion has used the case of blunt flow for illustration. The method is, however, applicable to the more typical case of laminar flow found in blood vessels.

Figure 7:
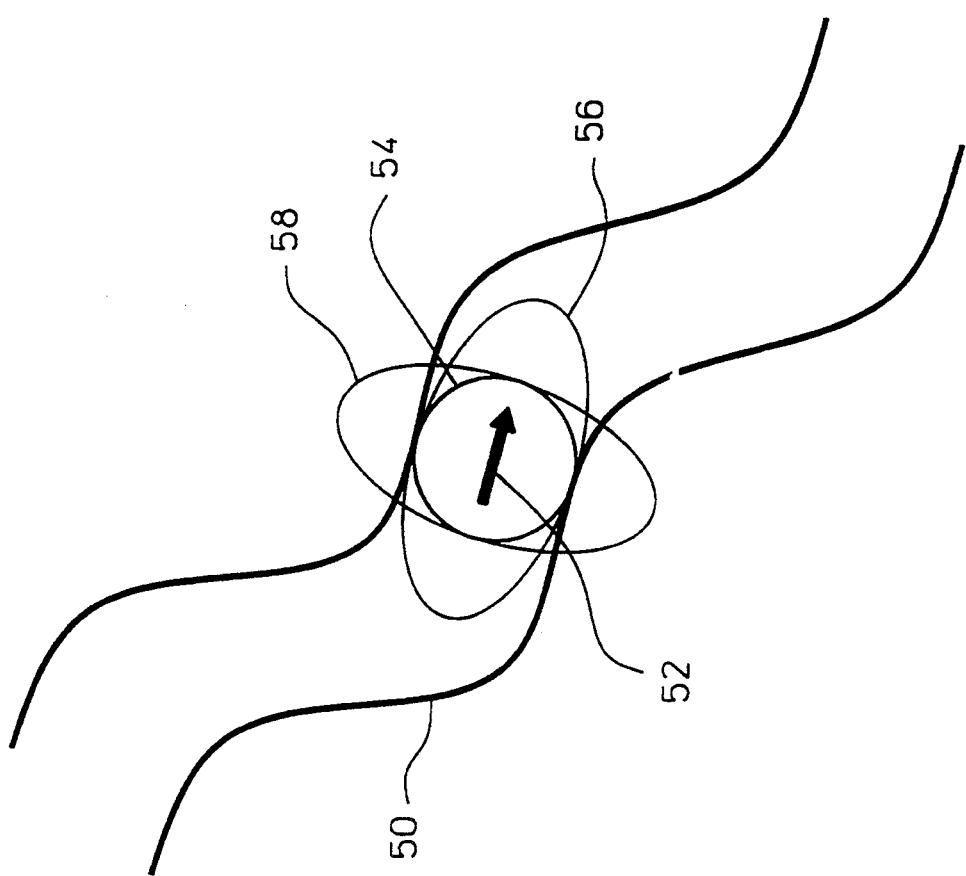
FIG. 7 illustrates a spherical interrogation volume in an artery and two ellipsoidal interrogation volumes used to determined the direction of blood flow.

FIG. 7 illustrates the SIV according to the invention and also illustrates the method according to the invention for determining the direction of flow of blood within a representative coronary artery 50. The local direction of flow of blood within the artery 50 is indicated by the arrow 52. FIG. 7 also shows a spherical interrogation volume 54 with the properties described above, which is focussed within the artery 50. As Eqns. 4 and 5 indicate, if the boundary of the interrogation volume, determined for example as the −6 dB boundary, is deformed so that the interrogation volume is ellipsoidal, a variation will be induced into the return signal so that the interrogation volume will become direction-dependent. The measured Doppler bandwidth of the back-scattered interrogation signal will then decrease as the direction of flow of the scattering particles within the fluid becomes more parallel to the long axis of the ellipsoid.

In FIG. 7, one ellipsoidal interrogation volume (EIV) 56 is shown closely aligned with the direction of blood flow 52 while another EIV 58 is shown with its long axis nearly perpendicular to the direction of flow 52. The return signal from the nearly perpendicular EIV 58 will show a much larger Doppler bandwidth than it will from the nearly aligned EIV 56. For any given eccentricity of the ellipsoid, it can be shown that the smallest Doppler bandwidth occurs when the long axis of the ellipsoid is parallel to the direction of flow.

This invention takes advantage of this phenomenon and provides a method for determining the direction of blood flow within an interrogation volume as well as (or instead of) the magnitude of flow of the blood in the interrogation volume. If one first wishes to measure the flow magnitude, the ultrasonic array is first configured and excited so as to produce the SIV as described above and to focus it within the artery at a desired point of measurement.

As is well known, the ultrasonic signal that is back-scattered from within the interrogation volume is re-converted into an electrical signal because of the piezo-electric characteristics of the transducer elements, one or more of which may be used for the reconversion. The analog signal from the selected transducer elements is then sensed and, in most implementations, sampled to convert the signal into a digital form suitable for use in numerical calculations. The system (described in greater structural detail below) then determines the Doppler bandwidth of the return signal and the speed of flow in the manner explained above.

The SIV is then "deformed" into an EIV by changing the phasing of the various transducer elements in the array used to generate the ultrasonic signal. Of course, one may also choose to forego the SIV step or to perform it last, in which case one generates the EIV at the start. The eccentricity of the EIV may be chosen by experiment or through calculations so that there is a large enough change in the returned Doppler bandwidth as the ellipsoid is rotated.

In general, the greater the eccentricity of the ellipsoid is, the greater will be the induced variation in the return signal; the ability to detect when the long axis of the now anisotropic, EIV is aligned with the direction of flow, will also increase. The physical configuration of the transducer array and the different possibilities for changing the relative phases of the various transducer signals will limit one's choices of eccentricity for the EIV's. If the center of the ellipsoid is at a region where there is great curvature in the artery, the long axis itself may extend over a region in which the direction of blood flow changes radically.

The ellipsoidal interrogation volumes preferably have the same center of focus as the SIV itself. This ensures not only that the same region of the artery is being measured, but also that the determination of flow direction will be from the same point as the magnitude determination made using the SIV.

The Doppler bandwidth of the back-scattered ultrasonic signal for EIV's with the same center as the SIV (or as each other) is a function of the direction of the long axis of the ellipsoid and of the velocity of blood flowing through the EIV. Let $\bar{x}' = (x', y', z')$ be the direction of the long axis of the ellipsoidal interrogation volume. The Doppler bandwidth of the returned ultrasonic signal can then be expressed as:

$$F = F(\bar{x}', |V|).  \quad \text{Eqn. 9}$$

where $\bar{x}' = (x', y', z')$

Assume further that the magnitude of flow velocity $|V|$ through the interrogation volume remains substantially constant as the EIV is rotated about its center point. This means that Eqn. 9 can be further simplified such that the Doppler bandwidth of the return signal is a function of the long axis direction $\bar{x}'$ alone.

By changing the phasing of the transducer array, the long axis of the EIV may be rotated about the center point of the ellipsoid. As the ellipsoid is rotated, the measured Doppler bandwidth will itself change and will reach a minimum when the long axis $\bar{x}'$ is parallel to the direction of flow. Since the Doppler bandwidth F is a function of the three-dimensional vector $\bar{x}'$, any of a large number of known numerical optimization techniques, such as the Newton-Raphson techniques, may be used to control the manner in which the long axis is rotated in order to determine which orientation gives the minimum bandwidth. If the optimization method chosen requires one or more starting values for the vector $\bar{x}'$, these may be generated according to any known method, including simple random selection or arbitrary incremental changes in some predetermined direction.

As is mentioned above, known numerical techniques may also be used to calculate the Doppler bandwidth of the return signal for any given interrogation volume. In order to determine the Doppler bandwidth, however, many values will normally need to be accumulated in order to get a reliable estimate of the bandwidth of the return signal. The speed at which one can accumulate measurements will typically be the same as the pulse rate of the ultrasonic transducer array itself. For each of the ellipsoidal interrogation volumes, it will therefore be necessary to hold the volume fixed long enough to accumulate a sufficient number of measurements before taking the next step in the optimization routine, that is, before moving the EIV to a new orientation. The proper speed at which one rotates the ellipsoidal interrogation volumes may be determined by experiment and by incorporating any prior knowledge of the flow characteristics of the fluid.

Once the minimum value of the Doppler bandwidth of the return signal is sensed, the direction of flow may be assumed to be the same as the direction of the long axis of the ellipsoid that provided the minimum value. Since this direction is known (x', y', z') as well as the center point of the ellipsoid (the focal point of the interrogation volume), one will have determined the direction of flow in that interrogation volume. If one has already measured this same region using the spherical interrogation volume, one will also have an accurate measure of $|V|$, the magnitude of the flow velocity. Of course, since the ellipsoidal interrogation volumes may be used to determine direction of flow (and thus the angle between the direction of flow and the line of sight or interrogation direction of the transducer array), normal Doppler techniques may then be applied regardless of the SIV in order to get an estimate of the flow.

Figure 8:
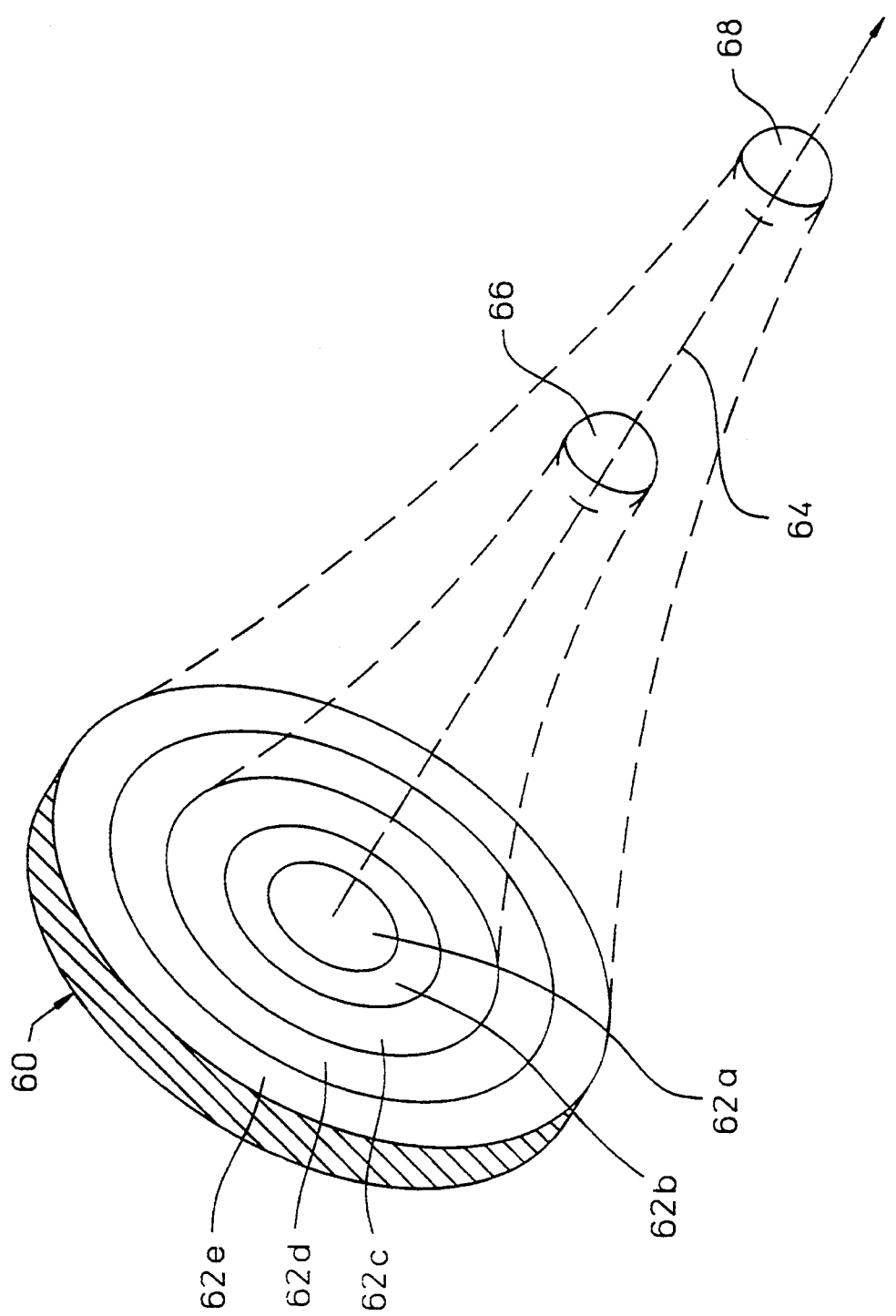
FIG. 8 illustrates an annular array of ultrasonic transducer elements that can be used to generate the SIV according to the invention.

FIG. 8 illustrates an array 60 of annular piezoelectric ultrasonic transducer elements 62a, 62b, 62c, 62d, and 62e. In the illustrated example, five annular transducer elements are shown, but more or fewer transducer elements may be used depending on the needs of any given application. For example, increasing the number of transducer elements while keeping the diameter of the array constant will in general increase the range over which equal-size spherical interrogation volumes may be produced, but it will also increase the complexity of the circuitry that excites and phases the various transducer elements.

In the simplest case, the surface of the array 60 is substantially flat, although it is also possible to have a concave array and still be able to create a spherical interrogation volume. The annular array 60 generates interrogation volumes that are focussed on the line of the interrogation direction 64, which is substantially perpendicular to the array 60 and passes through its center point. The focal distance of the array 60 can be adjusted in a known manner by changing the number of transducer rings 62a-62e that are excited at the same time; starting with the two center transducer elements 62a, 62b, each time another concentric transducer ring is added, the aperture of the array 60 is increased. In FIG. 8, one SIV 66 is shown being generated by the three innermost transducer elements 62a-62c. Another SIV 68 that is farther away from the array 60 is created when all five transducer elements 62a-62e are excited.

The distance at which the interrogation volume is focused is also a function of the relative delay of excitation of the various transducer elements. Delay focusing is known in the art and it is known that by changing the relative phasing of the signals from the transducer elements, the results of the constructive interference that arises moves the focus of the array in and out. Using a smaller aperture (fewer concentric annular transducer elements), one is able to focus at a shorter distance while still maintaining the same f-number. As is described above, the invention is unique compared to what is known in that it generates the interrogation volume with the lateral dimension substantially equal to the range and then evaluates flow based on the Doppler bandwidth of the return signal to achieve isotropism.

Figure 9:
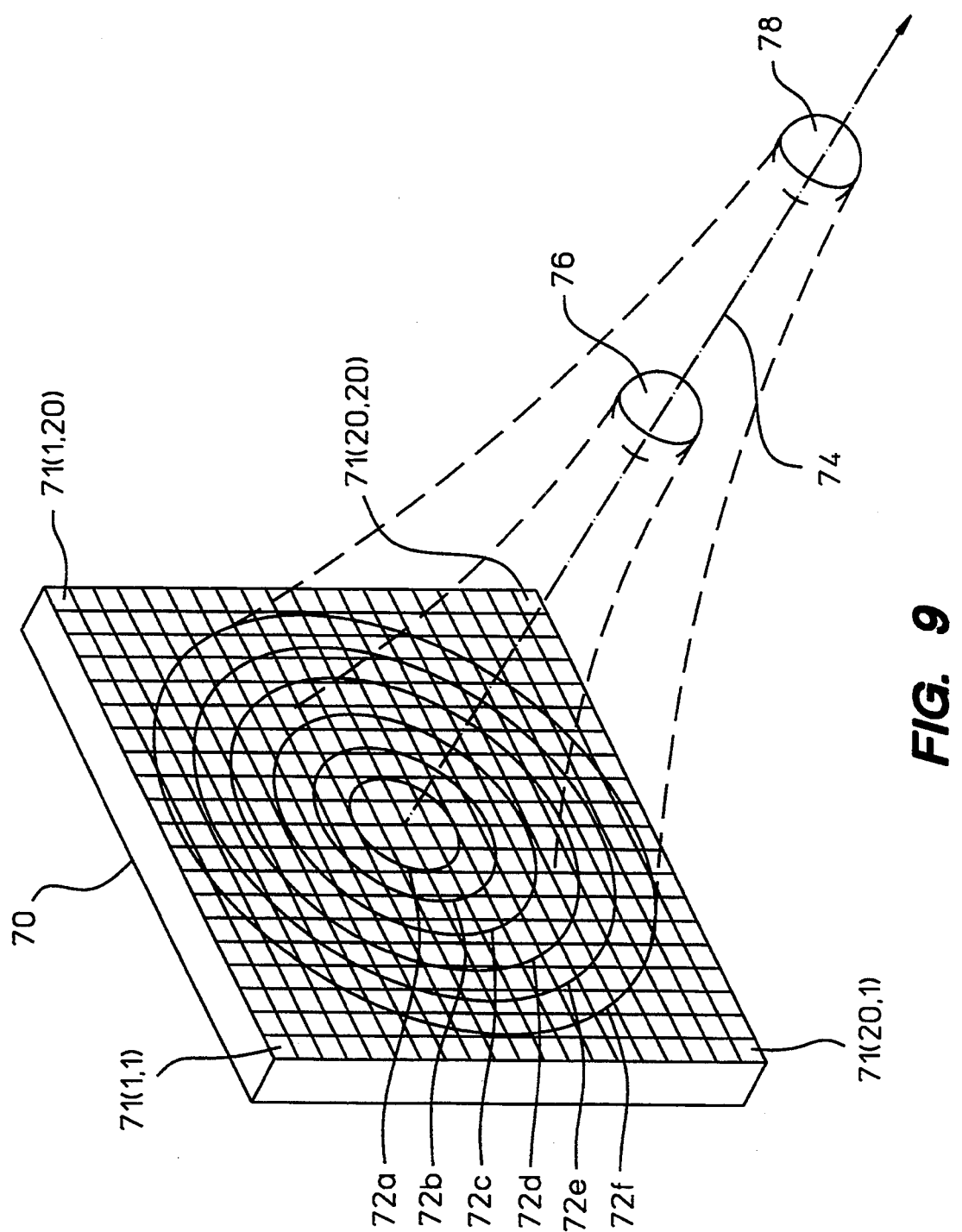
FIG. 9 illustrates a two-dimensional phased array of ultrasonic transducer elements that can generate the SIV.

FIG. 9 illustrates a 2-D phased array 70 of ultrasonic transducer elements. In the illustrated example, the array consists of 400 transducer elements arranged as a 20-by-20 matrix, whose corner transducer elements are labeled as 71(1, 1), 71(1, 20), 71(20, 1), and 71(20, 20). The number of transducer elements used in any given application will depend on the desired degree of beam-forming and other factors such as allowable manufacturing complexity and cost.

Concentric rings 72a-f are shown superimposed on the face of the array 70 only for the purpose of explanation. According to the invention, the individual transducer elements of the 2-D phased array 70 are excited in such a way that the array 70 can simulate a system of annular transducer elements, but is also able to simulate other apertures. In operation, in order to simulate the innermost transducer element (within the ring 72a), all of the transducer elements within the region marked by the ring 72a, or that have at least some predetermined portion within the ring, are excited simultaneously with substantially identical excitation signals. Similarly, any other annular region is simulated by exciting simultaneously those transducer elements that lie sufficiently within the corresponding annular region on the face of the array 70.

In the illustrated example, the 2-D phased array 70 is used to simulate on-axis focusing like that of the annular array shown in FIG. 8. Consequently, along the interrogation direction 74, different spherical interrogation volumes 76, 78 may be created depending on the diameter of the "aperture" created by the outermost simulated transducer "ring."

One of the advantages of the 2-D phased array 70 is that the number and diameters of the annular regions can be changed through a simple change in the electrical excitation signals, with no need for any mechanical changes. An additional advantage of the 2-D array 70 is that it also makes it possible not only to change the focal distance of the array but also to change the interrogation direction 74 and to modulate the eccentricity of the interrogation volumes. Depending on the physical properties of the transducer elements in the array 70, known analytical and numerical techniques, simulation, and experimentation can be used to determine excitation signals for the transducer elements that produce signals that constructively interfere to create and rotate ellipsoidal interrogation regions, as well as interrogation regions with other shapes.

Figure 10:
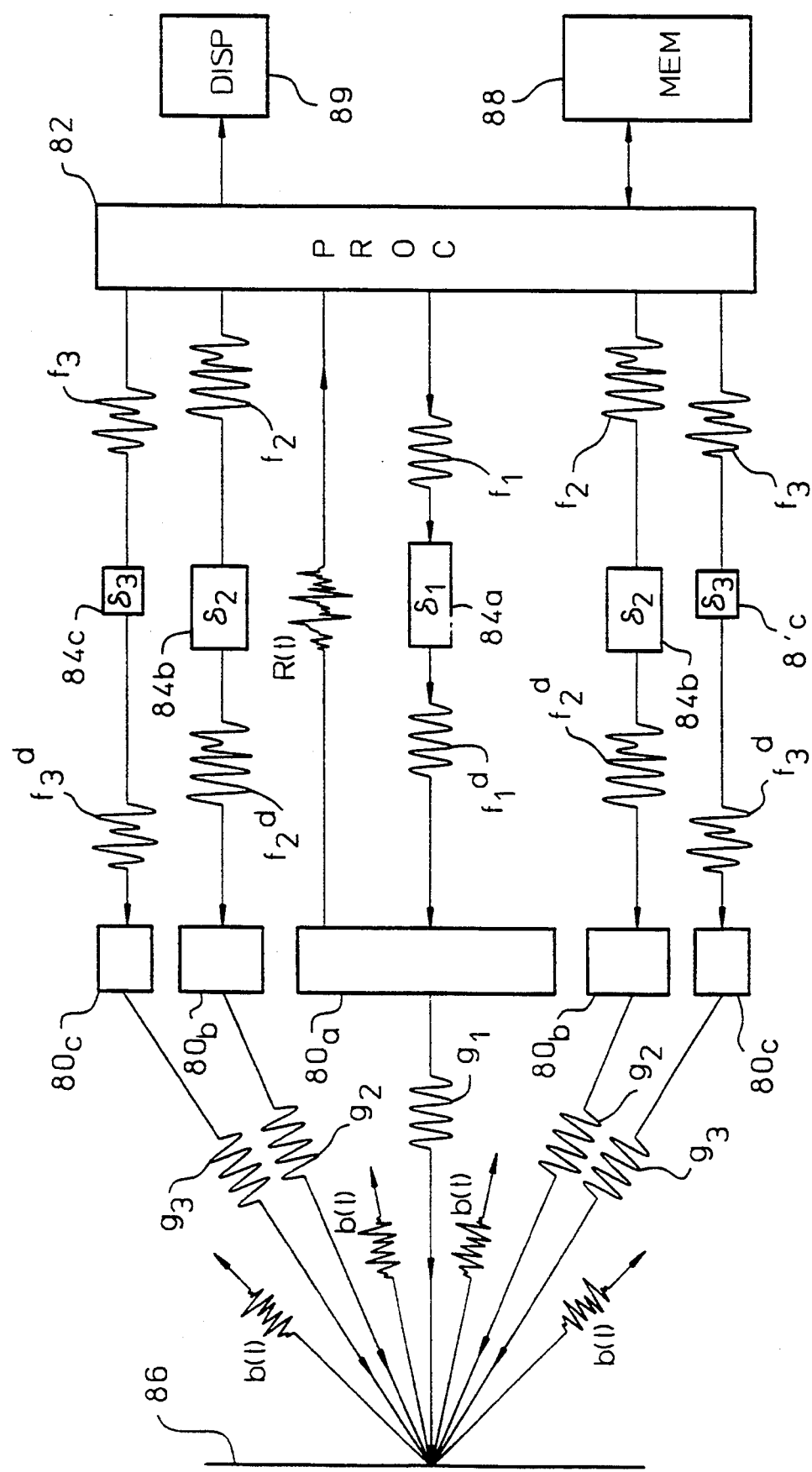
FIG. 10 shows a simplified block diagram of a system for generating the SIV using a three-ring annular array and the timing/phase relationships of the respective excitation signals for the different rings.

FIG. 10 is a schematic block diagram that shows the major components and signals of a system for measuring flow using an ultrasonic spherical or ellipsoidal interrogation volume. In FIG. 10, a simple 3-ring annular transducer array is shown only for purposes of easy explanation. In FIG. 10, the three elements of the array are labeled 80a, 80b, and 80c. Although a simple three-ring array is illustrated, the structure shown in FIG. 10 also applies in the more general case of a n-ring annular transducer array, or in the case of the 2-D phased array, for which the various excitation signals (described below) will be provided for each transducer in the array.

Conventional processing circuitry 82 generates electrical excitation signals $f_1$, $f_2$, $f_3$ as a sequence of pulses to drive the piezoelectric elements of the transducer array. In the simplest single-frequency or "monochromatic" case, each excitation signal will take the form $f_i(t) = E_i(t) \cdot \cos(\omega t)$, where $\omega$ is the same for all excitation signals. The excitation signals $f_1$, $f_2$, $f_3$ are time-delayed by amounts $\delta_1$, $\delta_2$, and $\delta_3$, respectively, either in separate conventional delay circuits 84a, 84b, 84c or by the processing circuitry 82 itself as it generates the excitation signals $f_1$, $f_2$, $f_3$. The different piezoelectric transducer elements 80a, 80b, 80c are excited by the respective delayed excitation signals $f_1^d$, $f_2^d$, $f_3^d$. Assuming that the excitation signals are single-frequency, the delayed excitation signals thus take the general form $$f_i^d = E_i(t) \cdot \cos[\omega \cdot (t - \delta_i)].$$

It is not necessary for the transducer excitation signals to be single-frequency; rather, as FIG. 10 shows for the excitation signals $f_2$ and $f_3$, the excitation signals may contain other frequency components so that the general form of the delayed excitation signals is:

$$f_i^d = (W_i, t, \delta_i)$$

where $W_i$ is a set of frequencies included in the spectrum of the respective excitation signal.

The transducer elements are excited by their respective input signals $f_i^d$ and emit corresponding ultrasonic output signals $g_1$, $g_2$, and $g_3$ that make up the interrogation signal and interfere with each other to focus the interrogation volume at a focal plane 86. Moving particles within the interrogation volume back-scatter the ultrasonic signal as a return signal $b(t)$. The back-scattered ultrasonic return signal is converted by one or more of the piezoelectric transducer elements 80a, 80b, 80c into the electrical return signal $R(t)$, which is a composite of the electrical return signals generated by each of the transducer elements in the array. After range gating, the Doppler bandwidth calculations are carried out in the processing circuitry 82. In a multi-element transducer, conventional beam-forming techniques are preferably used to combine the individual RF signals at each element in to the composite RF signal $R(t)$ for range-gating.

The processing circuitry 82 may contain or be connected to conventional signal generation and conditioning circuitry in order to create the excitation signals $f_1$, $f_2$, $f_3$ as a sequence of pulses that are repeated at a predetermined rate. Similarly, the processing circuitry 82 may contain or be connected to conventional receiving and conditioning circuitry that carries out such functions as pre-amplification, sampling, and analog-to-digital conversion, which transforms the return signals, either individually or as the composite $R(t)$, from the transducer elements into numerical values suitable for use in the calculations of the Doppler bandwidth of the composite return signal.

A memory circuit 88 is either connected to or is contained within the processing circuitry 82. The memory circuit 88 is used to accumulate the successive values of the return signal that are used to estimate the Doppler bandwidth of the return signal, which forms the basis of the flow measurements in this invention. The memory circuit 88 may also be used, for example, to digitally store signal profiles that the processing circuitry 82 uses to generate the excitation signals $f_1$, $f_2$, $f_3$. The flow magnitude or direction results may be displayed to the user on any conventional alphanumerical, graphical or other display device 89 that is driven by an output of the processing circuitry 82. The output results may also be passed on to additional processing, evaluation, or application circuitry.

The invention involves generating a spherical interrogation volume in order to determine flow magnitude independent of direction. The ultrasonic transducer output signals $g_1$, $g_2$, $g_3$ must therefore have signal forms that constructively interfere to create the spherical interrogation volume. In the preferred embodiment shown in FIG. 9 with the 2-D phased array, the excitation signals to the transducer elements may also have such signal waveforms that the constructive interference of the ultrasonic output signals from the transducer elements creates ellipsoidal interrogation volumes.

As is mentioned above, the envelope $E(t)$ of the output signals from the ultrasonic transducer elements is such that, for an SIV, the range dimension is set equal to the azimuth and elevation dimensions of the interrogation volume. The output signal from a transducer element will be substantially the same as its excitation signal only if the transducer is sufficiently "fast." In general, however, the output signal from a transducer element will not be the same as the excitation signal that forms the electrical input to the piezoelectric transducer element.

The "slower" a transducer element is, the greater the degree of change will be, especially for input excitation signals that have more than one component frequency. As is well known, the characteristics of the output signal will depend on the impulse response characteristics of the corresponding transducer. Since one knows or can calculate the characteristics of the output signal that are required to generate the spherical or elliptical interrogation volumes according to the invention, it is possible to determine the required excitation signals either theoretically by deconvolution (assuming one knows or can estimate the impulse response function of each transducer), by simulation, or by experimentation. The parameters necessary to generate the corresponding signals may be stored in the memory circuit 88 for use by the processing circuitry 82 in generating the excitation signals $f_1, f_2, f_3$, not only for a given SIV, but also for the position in space of the SIV, or the position, orientation, and eccentricity of elliptical interrogation volumes.

Figure 11:
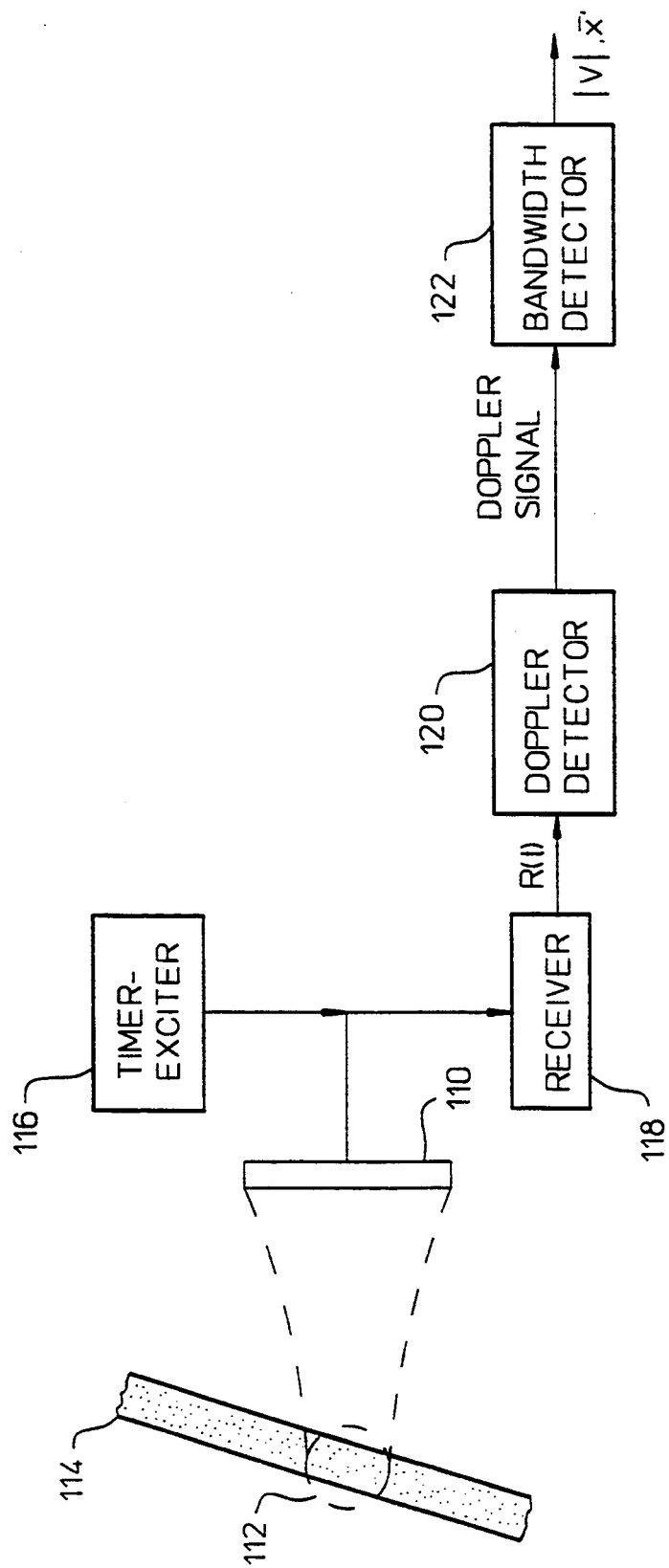
FIG. 11 is a block diagram that shows the main functional components of the flow measurement system according to the invention.

FIG. 11 is a block diagram that shows the main functional components of the flow measurement system according to the invention. A transducer 110 (preferably the 2-D phased array) focuses an interrogation volume 112 (depending on the flow characteristic to be measured, either an SIV or an EIV) within a vessel such as an artery 114. Particles such as red blood cells in the artery scatter the ultrasonic interrogation signal back to the transducer 110; in the figure, these particles are indicated by small "dots" within the artery 114.

A timer-exciter circuit 116 is electrically connected to apply excitation signals to the elements of the transducer 110. The timer-exciter circuit 116 applies these excitation signals to the transducer at a constant pulse repetition frequency and with waveform characteristics described above, so that the two-way pulse length and beam pattern result in the interrogation volume 112 being spherical or ellipsoidal, or at least approximately so.

A conventional receiver 118 senses the back-scattered signal to the transducer elements and, in a known manner, combines the individual RF signals from each transducer element into the composite RF return signal $R(t)$ after conventional range-gating.

A conventional Doppler detector block 120 receives the composite signal $R(t)$ as an input signal and, using known technology, outputs a signal corresponding to the Doppler shift of the return signal $R(t)$. A bandwidth detector 122 evaluates this Doppler signal using known techniques to determine its bandwidth and, after performing the calculations described above, outputs for further processing or display a signal corresponding to either the magnitude of flow velocity or the direction of fluid flow.

The receiver 118 will typically be an analog device and will preferably contain circuitry for carrying out such functions as pre-amplification, sampling, and analog-to-digital conversion (if the Doppler detector 120 has a digital input), in order to transform the back-scattered signals from the transducer elements into analog quantities or numerical values suitable for use in the determination of the Doppler shift. The timer-exciter 116, the receiver 118, the Doppler detector 120, and the bandwidth detector 122 are all included in the processing circuitry 82 shown in FIG. 10. Furthermore, the time-exciter 116 preferably contains or implements the same functions as the delay circuits 84a, 84b, 84c.

The timer-exciter 116, the Doppler detector 120, and the bandwidth detector 122 may be implemented as separate components, but they are preferably all implemented digitally (except, if needed, digital-to-analog conversion of the excitation signals, which can be done using conventional conversion circuitry). In such case, these devices may be implemented using a known digital processor.

We claim:

1. A method for measuring blood flow within a blood vessel or organ comprising the following steps:
    A. repeatedly applying to each of a plurality of piezoelectric transducer elements a corresponding pulsed electrical transmit signal;
    B. in the transducer elements, sensing a receive signal that is back-scattered from blood within the blood vessel or organ;
    C. electrically shaping and phasing the transmit and receive signals to generate a substantially spherical and isotropic interrogation region within which blood flow is to be measured;
    D. for each application of the pulsed electrical excitation signals, sensing an ultrasonic return signal that is back-scattered from particles within the interrogation region;
    E. converting the sensed ultrasonic return signals into a corresponding composite electrical return signal;
    F. measuring Doppler shift of the composite electrical return signal and generating a corresponding detected Doppler signal;
    G. measuring the bandwidth of the detected Doppler signal;
    H. determining a proportionality factor that is proportional to a beam width of the interrogation region; and
    I. outputting a representation of a magnitude of flow velocity as a predetermined function of the measured bandwidth of the detected Doppler signal, the predetermined function comprising scaling the beam width by the proportionality factor.

2. A method as defined in claim 1, in which the step of shaping and phasing the electrical transmit and receive signals includes generating the transmit and receive signals with a range dimension of the interrogation region substantially equal to an elevational dimension and an azimuthal dimension.

3. A method as defined in claim 1, in which the predetermined blood flow characteristic is the direction of blood flow, comprising the following additional steps:
    A. shaping and phasing the electrical transmit and receive signals to the transducer elements so that the interrogation region is substantially ellipsoidal with a long axis;
    B. generating a plurality of the ellipsoidal interrogation regions with different directions of their respective long axes; and
    C. outputting as the representation of the flow direction the direction of the long axis of the ellipsoidal interrogation region for which the measured bandwidth is a minimum.

4. A method as defined in claim 3, in which the step of shaping and phasing the transmit and receive signals includes differential phasing of a plurality of transducer elements arranged as a two-dimensional phased array.

5. A method for measuring the magnitude of velocity of blood flow in a blood vessel or organ comprising the following steps:
    A. repeatedly applying to each of a plurality of piezoelectric transducer elements a corresponding pulsed electrical transmit signal;
    B. in the transducer elements, sensing a receive signal that is back-scattered from blood within the blood vessel or organ;
    C. electrically shaping and phasing the transmit and receive signals to generate a substantially spherical and isotropic interrogation region within which blood flow is to be measured, with a range dimension of an interrogation region substantially equal to an elevational dimension and an azimuthal dimension;

D. for each application of the pulsed electrical transmit and receive signals, sensing an ultrasonic return signal that is back-scattered from particles within the interrogation region;

E. converting the sensed ultrasonic return signals into a corresponding composite electrical return signal;

F. determining a proportionality factor that is proportional to a beam width of the interrogation region;

G. measuring Doppler shift of the composite electrical return signal and generating a corresponding detected Doppler signal;

H. measuring the bandwidth of the detected Doppler signal; and

I. outputting a representation of a predetermined blood flow characteristic as a predetermined function of the measured bandwidth of the detected Doppler signal.

6. A system for measuring blood flow within a blood vessel or organ comprising:

A. an ultrasonic transducer with a plurality of piezoelectric transducer elements forming transducer means for generating a substantially spherical and isotropic ultrasonic interrogation region within which the blood flows;

B. timing and signal excitation and sensing means for repeatedly applying to each of the transducer elements a corresponding pulsed electrical transmit signal, for sensing a receive signal that is back-scattered to the transducer elements from blood within the blood vessel or organ, and for electrically shaping and phasing the transmit and receive signals to generate the interrogation region;

C. Doppler bandwidth detection means for detecting a bandwidth of a composite Doppler return signal corresponding to back-scattered return signals that have been back-scattered by particles in the blood; and D. processing means for generating a representation of a a magnitude of flow velocity as a predetermined function of the measured bandwidth of the detected Doppler signal, and for generating the representation of the magnitude of velocity by scaling the measured bandwidth by a proportionality factor, which is proportional to a beam width of the interrogation region.

7. A system for measuring blood flow within a blood vessel or organ comprising:

A. an ultrasonic transducer with a plurality of piezoelectric transducer elements forming transducer means for generating an ultrasonic interrogation region within which the blood flows, in which the interrogation region is substantially ellipsoidal with a long axis;

B. timing and signal excitation and sensing means for repeatedly applying to each of the transducer elements a corresponding pulsed electrical transmit signal, for sensing a receive signal that is back-scattered to the transducer elements from blood within the blood vessel or organ, and for electrically shaping and phasing the transmit and receive signals to generate the interrogation region;

C. Doppler bandwidth detection means for detecting a bandwidth of a composite Doppler return signal corresponding to back-scattered return signals that have been back-scattered by particles in the blood; and D. processing means:
1) for generating a representation of the direction of blood flow as a predetermined function of the measured bandwidth of the detected Doppler signal;
2) for controlling the timing and signal excitation and sensing means for generating a plurality of the ellipsoidal interrogation regions with different directions of their respective long axes; and
3) for outputting as the representation of the flow direction the direction of the long axis of the ellipsoidal interrogation region for which the measured bandwidth is a minimum.

8. A system as defined in claim 7, in which the transducer elements are as arranged as a two-dimensional phased array.

* * * * *